United States Patent [19]

Clegg et al.

[11] Plant 5,015

[45] Mar. 29, 1983

[54] ELM TREE

[76] Inventors: Samuel E. Clegg, Box 252, Plainfield, Ill. 60544; Charles P. McFarland, 603 Pfeffer Rd., Urbana, Ill. 61801

[21] Appl. No.: 258,592

[22] Filed: Apr. 29, 1981

[51] Int. Cl.[3] ..... A01H 5/12

[52] U.S. Cl. ..... Plt./51

[58] Field of Search ..... Plt./51

[56] References Cited

U.S. PATENT DOCUMENTS

P.P. 3,780 9/1975 Smalley et al. ..... Plt./51

OTHER PUBLICATIONS

Requirements for evaluating . . . , Pesticides Regulation Div., U.S.D.A., 9-24-64, 3 pp.

*Primary Examiner*—Robert E. Bagwill

*Attorney, Agent, or Firm*—Neuman, Williams, Anderson & Olson

[57] ABSTRACT

A new variety of elm tree characterized by its dark glossy green foliage that is retained until frost, excurrent habit of growth, wide crotches and rapid growth.

3 Drawing Figures

1

The present invention relates to a new and distinct variety of elm tree of the botanical genus known as Ulmus which was discovered by us as a selected seedling about 25 years ago in Aurora, Ill. This particular seedling was initially selected by us as possessing outstanding characteristics over other elm trees. This new elm tree possesses outstanding characteristics, such as rapid growth during its early years, dense glossy foliage that is retained until frost and crotches that are wider than is typical of other known elm trees.

We observed the tree for many years and because of its characteristics decided to propagate it.

Asexual reproduction of the new variety has been accomplished by soft-wood cuttings and budding on Siberian elm understock. Both methods of propagation have been successful and there are now approximately 250 trees.

The following are characteristics and distinctions of the new variety of elm tree, which characteristics and distinctions come true and are established and transmitted through succeeding propagation.

(1) Rapid growth during the tree's early years.

(2) Dense, glossy foliage that is held until frost.

(3) A branching habit with the branches joining the main trunk at a more obtuse angle that differs from typical elms wherein the branches join the main trunk at a more acute angle.

(4) Heavy callusing at the branch forks.

The drawings are photographic reproductions in color wherein

FIG. 1 shows front and back views of a leaf of the new elm tree of this invention;

FIG. 2 shows a branch of the elm tree of the invention having a number of leaves connected thereto; and FIG. 3 shows the heavy callusing at the axil of the branches of the elm tree of the invention.

The following is a detailed description of our new variety, with color terminology in accordance with The Royal Horticultural Society Color Chart:

2

Parentage: A hybrid seedling of the Red or Slippery Elm (*Ulmus fulva* [Michx.]) and the Siberian Elm (*Ulmus pumila* [Linn.])

Propagation: Holds its distinguishing characteristics through succeeding propagations by softwood cuttings and bud grafting.

Locality where grown and observed: Numerous nurseries throughout the Midwest, including Ohio, Illinois, Minnesota, Iowa, Missouri, and Oklahoma.

Tree: Rapid growing; parabolic in shape; branching is excurrent.

*Trunk.*—Stocky, slightly fissured. Color — Dark Grey Green (R.H.S. 198A).

*Branches.*—Slender; smooth. Color — Grey Green (R.H.S. 198D). Lenticels — Moderately abundant. Heavily callused at axis; branching angle at the axis is approximately 55°.

Foliage: Lustrous dark green leaf; abundant; about 9 centimeters long; about 5 centimeters wide; cordante — acuminate; double serrated; moderately scabrous.

*Color.*—Upper surface dark green (approximates R.H.S. 137A); lower surface is lighter yellow green (approximates R.H.S. 147B). Fall color not significant. (Approximates an average yellow similar to R.H.S. 11A.)

Flower buds:

*Hardiness.*—Hardy to −25° F.;
*Color.*—Grey Orange (R.H.S. 176B.)
*Surface.*—Slightly scabrous (denotes *Ulmus fulva* parentage).

Flowers:

*First bloom.*—About April 10;
*Quantity.*—Abundant.

Fruits: Ripen about May 15 to 20 in Northern Illinois.
*Abundance.*—Very abundant.

We claim:

1. A new and distinct variety of elm tree, substantially as herein shown and described, characterized further as to its lustrous dark green foliage that is retained until frost, excurrent habit of growth, rapid rate of growth and with the branches joining the main trunk at an angle more obtuse than is common in other elm trees.

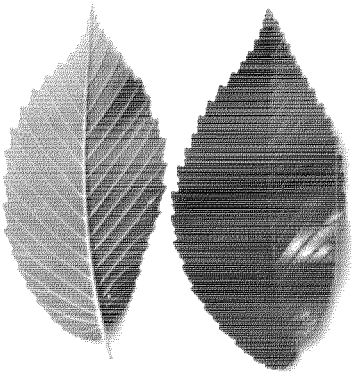
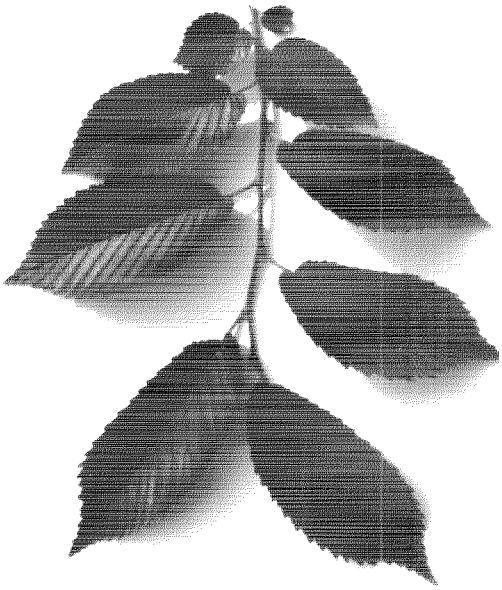

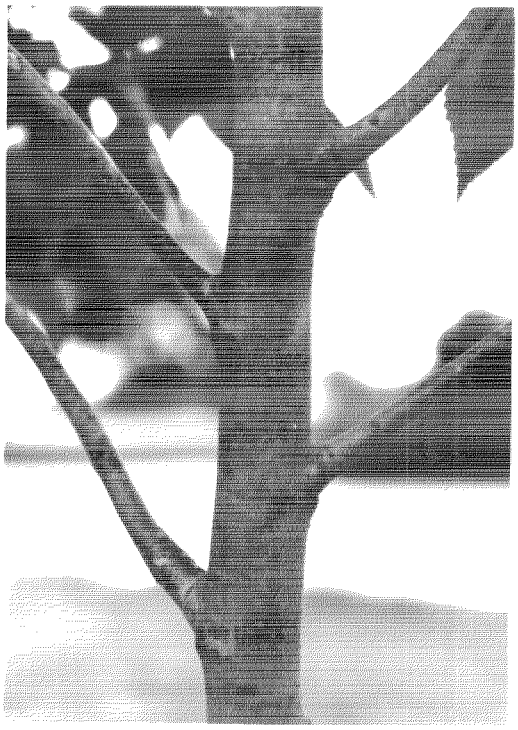

* * * * *